United States Patent
Gil et al.

(10) Patent No.: US 12,287,270 B2
(45) Date of Patent: Apr. 29, 2025

(54) BATTERY PACK INCLUDING GAS SENSING APPARATUS USING MIE SCATTERING AND GAS DETECTION METHOD USING THE SAME

(71) Applicant: LG ENERGY SOLUTION, LTD., Seoul (KR)

(72) Inventors: Gi Moon Gil, Daejeon (KR); Jee Ho Kim, Daejeon (KR)

(73) Assignee: LG ENERGY SOLUTION, LTD., Seoul (KR)

( * ) Notice: Subject to any disclaimer, the term of this patent is extended or adjusted under 35 U.S.C. 154(b) by 645 days.

(21) Appl. No.: 17/627,329

(22) PCT Filed: Oct. 7, 2020

(86) PCT No.: PCT/KR2020/013611
§ 371 (c)(1),
(2) Date: Jan. 14, 2022

(87) PCT Pub. No.: WO2021/071217
PCT Pub. Date: Apr. 15, 2021

(65) Prior Publication Data
US 2022/0276146 A1 Sep. 1, 2022

(30) Foreign Application Priority Data
Oct. 10, 2019 (KR) .......... 10-2019-0125101

(51) Int. Cl.
*G01N 15/06* (2024.01)
*G01N 33/00* (2006.01)
(Continued)

(52) U.S. Cl.
CPC ......... *G01N 15/06* (2013.01); *G01N 33/0027* (2013.01); *H01M 10/488* (2013.01); *H01M 50/204* (2021.01); *G01N 15/075* (2024.01)

(58) Field of Classification Search
None
See application file for complete search history.

(56) References Cited

U.S. PATENT DOCUMENTS

| | | |
|---|---|---|
| 9,553,465 B2 | 1/2017 | Raghavan et al. |
| 2006/0286441 A1 | 12/2006 | Matsuoka et al. |

(Continued)

FOREIGN PATENT DOCUMENTS

| | | | |
|---|---|---|---|
| CN | 101346619 A | 1/2009 | |
| CN | 105280974 * | 1/2016 | ............... A62C 3/07 |

(Continued)

OTHER PUBLICATIONS

International Search Report (PCT/ISA/210) issued in PCT/KR2020/013611 mailed on Jan. 12, 2021.

(Continued)

*Primary Examiner* — Amanda J Barrow
(74) *Attorney, Agent, or Firm* — Birch, Stewart, Kolasch & Birch, LLP

(57) ABSTRACT

A battery pack is capable of sensing the generation of a gas using Mie scattering, whereby it is possible to rapidly detect abnormality of the battery pack. In addition, whether a battery is abnormal is determined in consideration of a gas generation time as well as the generation of the gas, whereby it is possible to rapidly detect whether the battery is abnormal.

8 Claims, 5 Drawing Sheets

(51) Int. Cl.
*H01M 10/48* (2006.01)
*H01M 50/204* (2021.01)
*G01N 15/075* (2024.01)

(56) References Cited

U.S. PATENT DOCUMENTS

| | | |
|---|---|---|
| 2009/0229250 A1 | 9/2009 | Yamakage et al. |
| 2012/0304903 A1 | 12/2012 | Lobo et al. |
| 2014/0303723 A1* | 10/2014 | Alkhatib ............... A61F 2/2418 623/2.17 |
| 2015/0303723 A1 | 10/2015 | Raghavan et al. |
| 2016/0133996 A1 | 5/2016 | Fukuhara |
| 2017/0229724 A1* | 8/2017 | Chen ................. H01M 8/04335 |
| 2017/0338527 A1* | 11/2017 | Walton .............. H01M 10/6568 |
| 2019/0046820 A1 | 2/2019 | Lee et al. |

FOREIGN PATENT DOCUMENTS

| | | |
|---|---|---|
| CN | 105393402 A | 3/2016 |
| JP | 1-104893 U | 7/1989 |
| JP | 3-44793 U | 4/1991 |
| JP | 2008-14715 A | 1/2008 |
| JP | 4227991 B2 | 2/2009 |
| JP | 2009-104808 A | 5/2009 |
| JP | 2013-514522 A | 4/2013 |
| JP | 2014-225386 A | 12/2014 |
| JP | 6122498 B2 | 4/2017 |
| JP | 2018-63765 A | 4/2018 |
| JP | 6414501 B2 | 10/2018 |
| JP | 2019-40814 A | 3/2019 |
| JP | 2019-159742 * | 9/2019 ............... G01J 1/02 |
| JP | 2019-159742 A | 9/2019 |
| KR | 10-2012-0111080 A | 10/2012 |
| KR | 10-2014-0085764 A | 7/2014 |
| KR | 10-1873910 B1 | 7/2018 |

OTHER PUBLICATIONS

Extended European Search Report for European Application No. 20874415.1, dated Jan. 29, 2024.

Li et al., "Design of in-situ Monitor System for Lithium-ion Battery based on Multifunctional fiber," Proceedings of SPIE, vol. 10846, 2018, 8 pages total.

* cited by examiner

【FIG. 3】
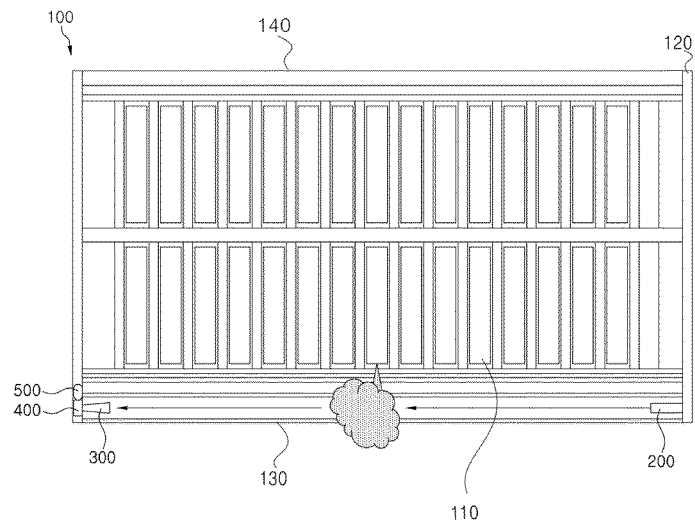
【FIG. 4】
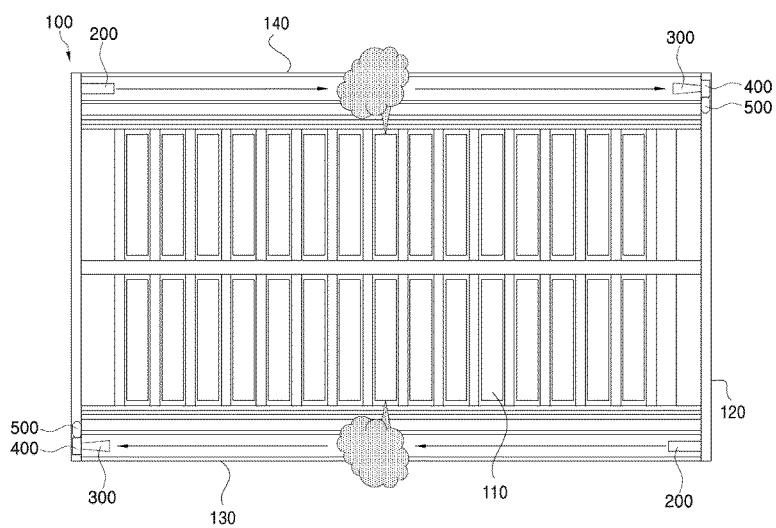

【FIG. 5】
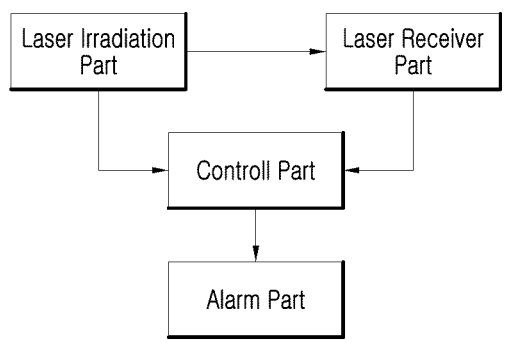
【FIG. 6】
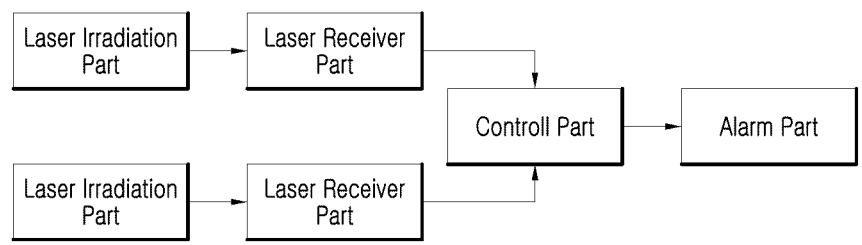

[FIG. 7]
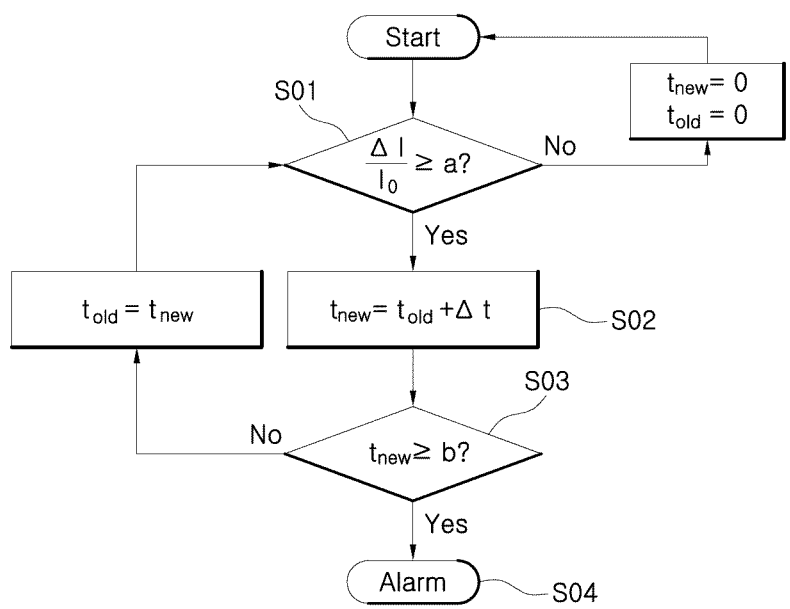
[FIG. 8]
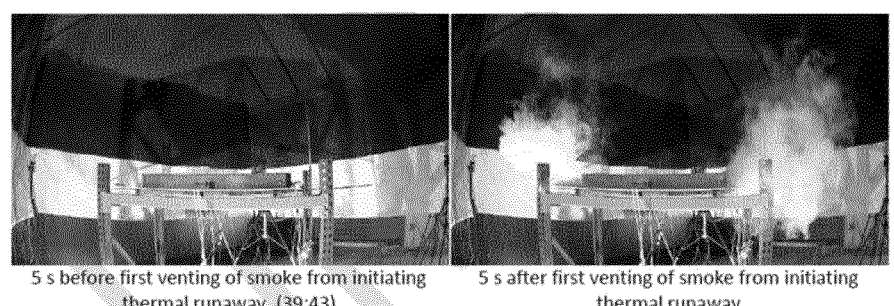

[FIG. 9]
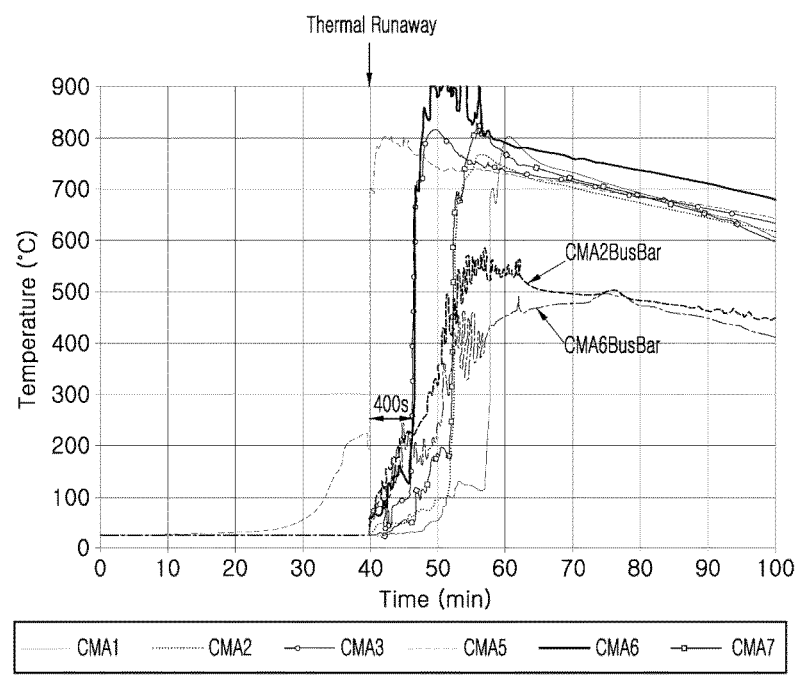

BATTERY PACK INCLUDING GAS SENSING APPARATUS USING MIE SCATTERING AND GAS DETECTION METHOD USING THE SAME

TECHNICAL FIELD

This application claims the benefit of priority to Korean Patent Application No. 2019-0125101 filed on Oct. 10, 2019, the disclosure of which is hereby incorporated by reference herein its entirety.

The present invention relates to a battery pack including a gas sensing apparatus using Mie scattering and a gas detection method using the same, and more particularly to a battery pack including a battery module including at least one unit cell, a rack housing configured to receive at least one battery module, a lower housing having an inner space in a form in which the upper part of the lower housing is open, the lower housing being configured to receive the battery module in the inner space, an upper housing coupled to the open upper part of the lower housing, the upper housing having an inner space configured to receive the battery module, and a laser unit disposed at one surface of the rack housing, the laser unit being configured to sense a gas using Mie scattering.

BACKGROUND ART

With technological development of mobile devices, such as mobile phones, laptop computers, camcorders, and digital cameras, and an increase in the demand therefor, research on secondary batteries, which are capable of being charged and discharged, has been actively conducted. In addition, secondary batteries, which are energy sources substituting fossil fuels causing air pollution, have been applied to an electric vehicle (EV), a hybrid electric vehicle (HEV), and a plug-in hybrid electric vehicle (PHEV), and therefore there increasing necessity for development of secondary batteries.

With an increase in demand for batteries and necessity for high-capacity batteries, various attempts to increase the capacities of the batteries have been made. Although there is a case in which the capacity of one battery cell is increased and used, a plurality of battery cells is electrically connected to each other so as to be used as a single battery in a general way. In general, it is preferable that a plurality of battery cells be electrically connected to each other in series or in parallel to form a battery module and a plurality of battery modules be received in a battery case so as to be used in the form of a battery pack.

For a high-capacity battery such a battery pack, however, it is difficult to cool the battery, compared to a single battery cell, whereby there is a higher danger of thermal runaway, fire, or explosion. In many cases, in order to prevent such a danger, a battery using high-capacity energy, such as large-capacity battery pack, includes a system configured to warn of or prevent the danger.

In connection therewith, a system configured to sense a gas in a battery may be provided, as shown in FIG. 1. FIG. 1 is a schematic view of a conventional gas sensor. In general, the gas sensor may be classified as a heat sensor, a smoke sensor, a heat and smoke combination sensor, or a flame sensor. The heat sensor operates in the case in which ambient temperature is equal to or greater than a predetermined rate of rise. The heat sensor operates only when the ambient temperature becomes a high temperature equal to or higher than a battery operation temperature. As a result, the heat sensor senses only a situation in which thermal runaway considerably advances or in which fire breaks out and informs of the result of sensing, whereby improvement in safety is not realized. In addition, for the smoke sensor, smoke must enter the interior of the smoke sensor, and therefore it takes time until a gas is generated in a battery cell and the gas is sensed. When the gas is sensed, therefore, heat may have already been transferred from one cell to a cell adjacent thereto, due to such a time difference, whereby thermal runaway may have occurred or a fire may have already broken out.

In order to solve this problem, Patent Document 1 discloses an optical method using an optical fiber sensor disposed in a battery, the optical fiber sensor being configured to receive input light and to provide output light, wherein the generation of a gas is determined based on the amount of the gas that is separated or dissolved in the battery. As a result, the system has disadvantages in that an error may occur due to the separated or dissolved gas and it takes a predetermined time until the gas is measured using the optical fiber sensor.

Therefore, there is a need for a battery safety improvement system capable of accurate informing of danger of a battery within a short time in order to improve battery safety.

PRIOR ART DOCUMENT

Patent Document (Patent Document 1) Japanese Registered Patent Publication No. 6414501

DISCLOSURE

Technical Problem

The present invention has been made in view of the above problems, and it is an object of the present invention to provide a battery pack including a gas sensing apparatus configured to directly and rapidly detect the generation of a gas using light and a gas detection method of the battery pack using the same.

It is another object of the present invention to provide a system capable of preventing false sensing of the generation of a gas to rapidly and accurately sense and inform of an abnormal state of a battery pack. It is a further object of the present invention to provide a battery pack capable of preventing fire or explosion due thereto.

Technical Solution

In order to accomplish the above objects, a battery pack according to the present invention includes at least one battery including at least one unit cell, a rack housing configured to receive the at least one battery module, a lower housing having an inner space in a form in which the upper part of the lower housing is open, the lower housing being configured to receive the at least one battery module in the inner space, an upper housing coupled to the upper part of the lower housing, the upper housing having an inner space configured to receive the at least one battery module, and at least one laser unit disposed at in the rack housing, the laser unit being configured to sense a gas using Mie scattering.

FIG. 2 is a conceptual view of Mie scattering in the present invention. Mie scattering is a phenomenon in which, in the case in which the wavelength of light is equal to or greater than the size of a particle, the light collides with the particle and is then scattered, as shown in FIG. 2, As can be seen from FIG. 2, light (indicated by an arrow in the figure) transmitted from a laser irradiation part 200 to a laser receiver part 300 collides with gas particles and is then scattered. Due to such a phenomenon, the density of the light received by the laser receiver part 300 is lower than the density of the light transmitted by the laser irradiation part 200. In addition, since the light collides with the gas particles and is then scattered, Mie scattering has no relation to wavelength and a difference in degree of scattering occurs depending on concentration or size of particles.

To this end, the laser unit may include a laser irradiator 200 formed at first surface of the rack housing, the laser irradiator being configured to irradiate laser light, a laser receiver part 300 configured to receive the laser light irradiated by the laser irradiator 200, the laser receiver being formed at a second surface of the rack housing opposite the laser irradiator 200, and a control part 400 configured to compare the intensity of the laser light received by the laser receiver 300 with a reference value in order to determine generation of a gas.

The gas may be directly detected through the laser irradiation part 200 and the laser receiver part 300 using the light, and the intensity of the received light may be compared to determine generation of the gas, whereby it is possible to securely recognize generation of the gas within a reduced time, compared to a conventional gas detection method.

At this time, the laser unit may irradiate laser light along the stacked surfaces of the unit cells. The laser unit may irradiate laser light in order to sense a gas generated in each unit cell. In addition, the laser unit may be disposed so as to detect gases generated in several unit cells.

The laser unit may include two or more laser units.

For example, for a battery pack in which battery modules are arranged in a line, one laser unit may be provided at one surface of the rack housing. In addition, one laser unit may be provided at one surface of the rack housing, and another laser unit may be provided at the other surface of the rack housing. Alternatively, for a battery pack in which battery modules are arranged in two or more lines, a laser unit may be disposed between respective lines of the battery modules, laser units may be disposed at opposite surface of the battery modules.

In the case in which two or more laser units are provided, as described above, the laser units may be located in a symmetrical fashion or as mirror images.

That the laser units are located in the symmetrical fashion means that the laser irradiation parts and the laser receiver parts are located at the same position between the laser units, i.e. the laser irradiation part 200 and the laser receiver part 300 located at one surface of the rack housing and the laser irradiation part 200 and the laser receiver part 300 located at the other surface of the rack housing are located opposite each other in a parallel state so as to correspond to each other. In addition, that the laser units are located as mirror images means that the laser irradiation part and the laser receiver part are located at the different positions, i.e. the laser irradiation part 200 located at one surface of the rack housing and the laser receiver part 300 located at the other surface of the rack housing are located in a parallel state so as to correspond to each other.

Also, in the case in which a plurality of laser units is provided, each of the laser units may include a laser irradiator 200, a laser receiver 300, and a control part 400. In addition, each of the laser units may include a laser irradiator 200 and a laser receiver 300, and a single control part 200 may process information received by the plurality of laser receiver parts 300.

The laser irradiator 200 may be configured to irradiate laser light having a wavelength equal to or less than the size of a gas particle generated in the battery pack. That is, the laser light irradiated by the laser irradiation part 200 may be irradiated with a wavelength equal to or less than the size of a gas particle generated in the battery pack. A gas particle used in the present invention means a gas particle formed using a burned gas as a precursor.

At this time, the gas particle may have a diameter of 0.1 μm to 10 μm.

In addition, laser light may be irradiated based on burned gases, such as hydrogen, carbon monoxide, carbon dioxide, methane, ethylene, ethane, and propylene, from which the gas particle is formed. The magnitude of the laser light may be decided based on at least one of the burned gases. Also, in the case in which a plurality of laser units is provided, the wavelengths of respective laser lights may be equal to or different from each other.

In addition, the laser unit may further include an alarm.

The alarm part may receive a signal generated by the control part and may inform a user of the signal. The alarm part may inform the user of the signal in any of various such as a sound or a display. In addition, the alarm part may constitute a portion of a battery management system (EMS) together with the control part.

The laser unit may be connected to the battery management system, which is configured stop the function of the battery pack. The function of the battery may be stopped by a safety device in the battery. Alternatively, the function of the battery may be stopped outside the battery. In addition, the laser unit may take a measure for preventing combustion or explosion of the battery pack.

In addition, the present invention provides a gas detection method of a battery pack, the gas detection method including 1) comparing the scattering ratio of laser light received by a laser receiver with a predetermined scattering ratio, 2) generating a signal when the scattering ratio of the received laser light is equal to or greater than the predetermined scattering ratio in step 1), and 3) sounding an alarm in response to a signal transmitted from the control part.

The scattering ratio of the laser light in step 1) may be a value obtained by dividing the intensity of the received laser light by the intensity of initial laser light set as a reference value. In addition, the predetermined scattering ratio in step may be an optical loss value based on gases detected in each battery pack. The optical loss value may be 2% to 5%. The optical loss value is based on a battery pack including seven battery modules, each battery module being constituted by eight general unit cells. The optical loss value may be changed depending on the kind and amount of burned gases that may be generated when a fire breaks out in the unit cells. In addition, the optical loss value may be changed depending on the length of the stacked surface of the battery pack, i.e. the movement distance of laser light. This may be set differently depending on the kind of the battery pack and the kind of the unit cells.

In addition, the gas detection method may further include a) adding a measured time value to a previous time value when the signal is generated in step 2 between step 2) and step 3).

In addition, the gas detection method may further include b) comparing a value obtained in step a) with a predetermined time and c) generating a signal when the obtained value is equal to or greater than the predetermined time in step b), step b) and step c) being performed between step a) and step 3).

This is performed in order to prevent the occurrence of a case in which conditions in the battery pack are changed depending on the measured time or a case in which a temporary error occurs in the value obtained by the laser receiver part. As described above, a time for which the intensity of laser light is measured may be measured, and the reference vale may be set differently based on the measured time. In addition, it may be determined that the gas has been generated only in the case in which the measured scattering ratio of the light is maintained for a predetermined time, as in step b) and step c), and the same may be transmitted to the alarm part. In addition, the function of the battery pack may be stopped.

The predetermined time may be 40 seconds to 60 seconds. The predetermined time is set based on a time of propagation of thermal runaway from one unit cell and a unit cell adjacent thereto. Consequently, the predetermined time may be changed depending on the kind of the stacked unit cells and the number of the stacked unit cells.

In addition, the present invention provides an electronic device using the gas detection method of the battery pack described above.

In the present invention, one or more constructions that do not conflict with each other may be selected and combined from among the above constructions.

DESCRIPTION OF DRAWINGS

FIG. 3 is a plan sectional view of a battery pack according to a first embodiment of the present invention.

FIG. 4 is a plan sectional view of a battery pack according to a second embodiment of the present invention.

FIG. 5 is a view showing the disposition of a laser unit according to a first embodiment of the present invention.

FIG. 6 is a view showing the disposition of a laser unit according to a third embodiment of the present invention.

FIG. 7 is a flowchart of a gas detection method of a battery pack according to the present invention.

FIG. 8 shows photographs of a fire outbreak test according to the present invention arranged over time.

FIG. 9 is a graph showing the results of the fire outbreak test according to the present invention.

BEST MODE

Figure 1:
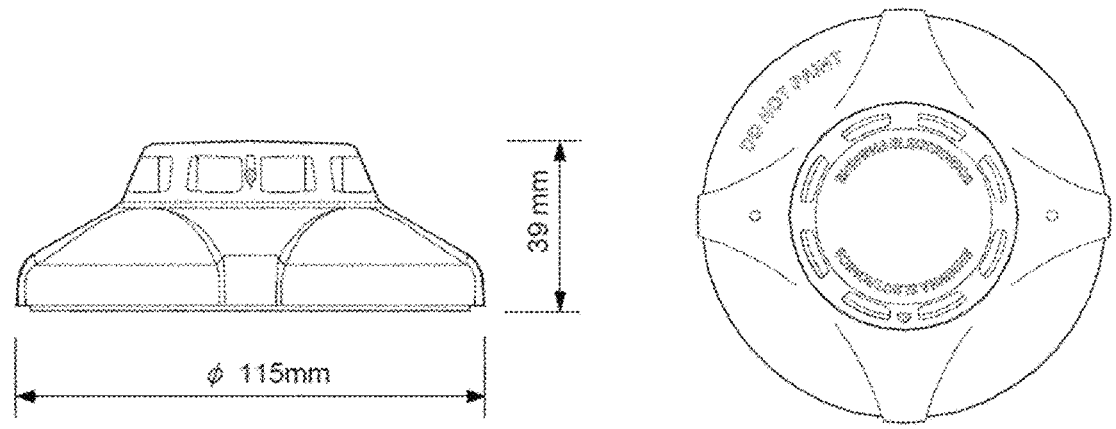
FIG. 1 is a schematic view of a conventional gas sensor.
Figure 2:
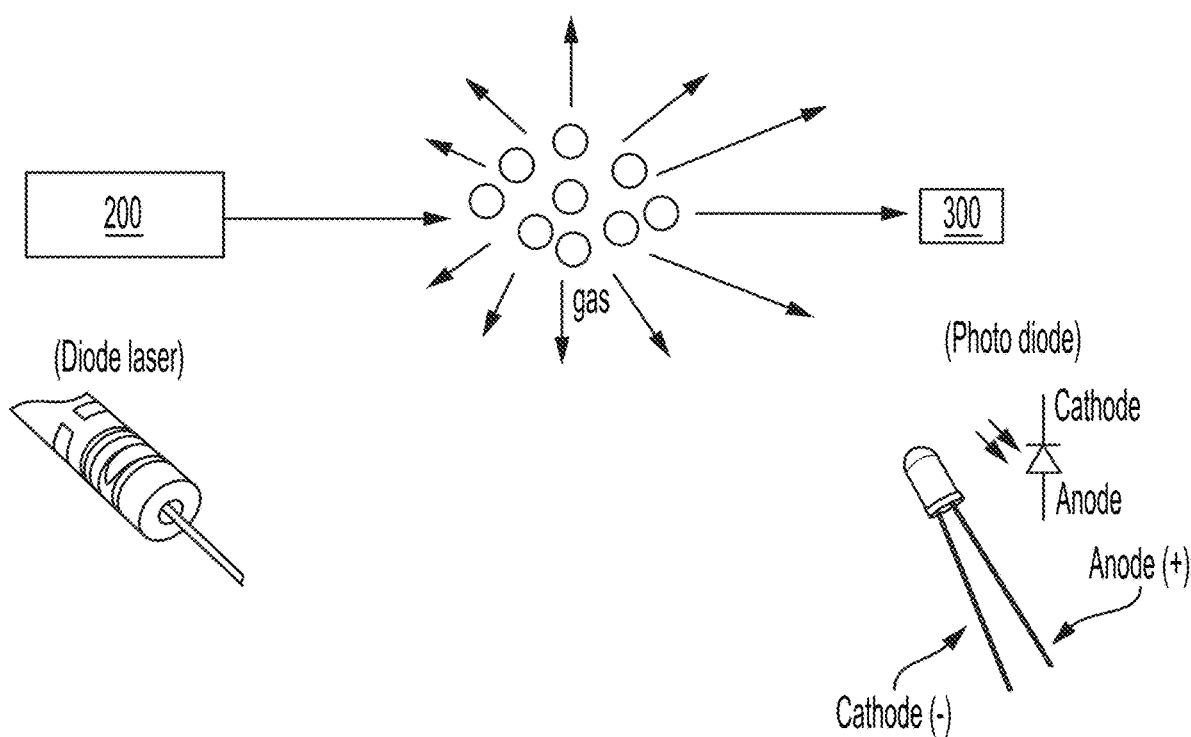
FIG. 2 is a conceptual view of Mie scattering in the present invention.

In the present application, it should be understood that the terms "comprises," "has," "includes," etc. specify the presence of stated features, numbers, steps, operations, elements, components, or combinations thereof, but do not preclude the presence or addition of one or more other features, numbers, steps, operations, elements, components, or combinations thereof.

In addition, the same reference numbers will be used throughout the drawings to refer to parts that perform similar functions or operations. In the case in which one part is said to be connected to another part in the specification, not only may the one part be directly connected to the other part, but also, the one part may be indirectly connected to the other part via a further part. In addition, that a certain element is included does not mean that other elements are excluded, but means that such elements may be further included unless mentioned otherwise.

Now, preferred embodiments the present invention will be described in detail with reference to the accompanying drawings such that the preferred embodiments of the present invention can be easily implemented by a person having ordinary skill in the art to which the present invention pertains. In describing the principle of operation of the preferred embodiments of the present invention in detail, however, a detailed description of known functions and configurations incorporated herein will be omitted when the same may obscure the subject matter of the present invention.

In addition, the same reference numbers will be used throughout the drawings to refer parts that perform similar functions or operations. In the case in which one part is said to be connected to another part in the specification, not only may the one part be directly connected to the other part, but also, the one part may be indirectly connected to the other part via a further part. In addition, that a certain element is included does not mean that other elements are excluded, but means that such elements may be further included unless mentioned otherwise.

Hereinafter, a battery pack including a gas sensing apparatus using Mie scattering according to the present invention and a gas detection method of the battery pack will be described with reference to the accompanying drawings.

FIG. 3 is a plan sectional view of a battery according to a first embodiment of the present invention, and FIG. 4 is a plan sectional view of a battery pack according to a second embodiment of the present invention.

Referring to FIG. 3, the battery pack 100 according to the first embodiment of the present invention is configured to have a structure in which a plurality of battery modules, each of which includes one or more unit cells, is received in a battery pack case and in which a laser irradiation part 200 is provided at one surface of a rack housing of the battery pack case, a laser receiver part 300 is provided at the other surface of the rack housing of the battery pack case, and a laser unit is disposed so as to irradiate laser light along stacked surfaces of the unit cells. The laser receiver part 300 is connected to a control part 400, and the control part 400 is connected to an alarm 500. Information about the laser light received by the laser receiver part 300 may be received by the control part 400, and the control part 400 may transmit determined information to the alarm part 500 such that the alarm part sounds an alarm.

The kind of the laser irradiation part 200 is not restricted as long as the laser irradiation part 200 is capable of irradiating laser light in one direction. In the case in which the size of the laser irradiation part 200 is too large, however, battery capacity may be reduced. Consequently, it is preferable that the laser irradiation part 200 be disposed at one surface of the battery pack in a surplus space thereof while having a size not greater than the size of one unit cell so as not to reduce the capacity of the battery pack. As an illustration, a diode-type laser irradiation part 200 may be used.

In addition, infrared rays, visible rays, ultraviolet rays, and X-rays may all be used as laser light irradiated by the laser irradiation part 200. In consideration of the size of gas particles generated from the battery, however, near infrared rays, visible rays, or ultraviolet rays are preferably used, and ultraviolet rays are more preferably used.

The laser receiver part 300 may be located at a region at which the laser receiver part 300 can receive laser light from the laser irradiation part 200. The laser receiver part 300 may generally be disposed so as to face the laser irradiation part 200. The kind of the laser receiver part 300 is not restricted as long as the laser receiver part 300 is capable of receiving laser light from the laser irradiation part 200 and transmitting the received laser light to the control part 400. In the case in which the size of the laser receiver part 300 too large, however, battery capacity may be reduced. Consequently, it is preferable that the laser receiver part 300 be disposed at one surface of the battery pack in the surplus space thereof while having a size not greater than the size of one unit cell so as not to reduce the capacity of the battery pack. As an illustration, a diode-type laser receiver part 300 may be used.

The intensity of laser light received by the laser receiver part 300 is transmitted to the control part 400 through an electrical signal, and the control Part 400 compares a received value with a pre-input value. In the case in which a desired result value is obtained, the control part 400 transmits the result value to the alarm part 500.

The control part 400 and/or the alarm part 500 may be mounted at the battery pack 100, and may be mounted at a place other than the battery pack 100. In the case in which the control part 400 and/or the alarm part 500 is mounted at the battery pack 100, the control part 400 and/or the alarm part 500 is located at one surface of the battery pack 100 in the surplus space thereof so as not to reduce the capacity of the battery pack 100. In addition, it is also preferable that the size of the control part 400 and/or the alarm part 500 be small as long as it is possible to perform a necessary function.

In the case in which the control part 400 and/or the alarm part 500 is mounted at a place other than the battery pack 100, on the other hand, the size of the control part 400 and/or the alarm part 500 is not limited, and the control part 400 and/or the alarm part 500 may correspond to a portion of a battery management system (BMS).

The laser irradiation part 200 and the laser receiver part 300 may be located at one side surface of the battery pack 100, as in the first embodiment of FIG. 3, or the laser irradiation part 200 and the laser receiver part 300 may be disposed between columns in which the battery modules or the unit cells are stacked, i.e. such that light from the laser irradiation part 200 is irradiated to one side of each of the plurality of battery modules or unit cells stacked the battery pack 100 and the irradiated light is received by the laser receiver part 300, as in the laser irradiation part 200 and the laser receiver part 300 of FIG. 3.

In addition, the battery pack according to the present invention may include two or more laser irradiation parts 200, two or more laser receiver parts 300, two or more control parts 400, and two or more alarm parts 500, as in the second embodiment of FIG. 4. In this case, the two laser irradiation parts 200 and the two laser receiver parts 300 may be located at the same position, or may be located at the different positions, as shown in FIG. 4. That is, the laser irradiation part 200 and the laser receiver part 300 located at one surface of the rack housing and the laser irradiation part 200 and the laser receiver part 300 located at the other surface of the rack housing may be located opposite each other in a parallel state so as to correspond to each other, or the laser irradiation part 200 located at one surface of the rack housing and the laser receiver part 300 located at the other surface of the rack housing may be located in a parallel state so as to correspond to each other, as shown in FIG. 4. In the case in which the laser irradiation part 200 and the laser receiver part 300 are disposed at the same position, information received by the laser receiver part 300 may be compared in order to reduce an error. In addition, since the amount of gas that can be sensed by the laser receiver part 300 may be limited in a battery pack including a plurality of battery modules, the laser irradiation part 200 and the laser receiver part 300 may be disposed at opposite side surfaces of the rack housing in different directions in order to supplement this.

The battery pack may have a structure in which the laser irradiation part 200 and the laser receiver part 300 are connected to a single control part 400 and the control part 400 is connected to the alarm part 500 based on received information structure in which a pair of laser irradiation parts 200 and a pair of laser receiver parts 300 are provided for a single control part 400 and a single alarm part 500 may be applied not only to a single laser unit but also to a plurality of laser units.

FIG. 5 is a view showing the disposition of a laser unit according to a first embodiment of the present invention.

As can be seen from FIG. 5, in the laser unit according to the first embodiment of the present invention, a laser irradiation part transmits laser light to a laser receiver part, and the laser irradiation part and the laser receiver part transmit information to a control part in order to sound an alarm based thereon. The control part may be connected to a pair of laser irradiation parts and a pair of laser receiver parts.

A structure in which a single control part and/or a single alarm part is provided together with a single laser irradiation part and a single laser receiver part may be applied to a laser unit according to a second embodiment in addition to the laser unit according to the first embodiment.

FIG. 6 is a view showing the disposition of a laser unit according to a third embodiment of the present invention.

In the laser unit according to the present invention, a plurality of pairs of laser irradiation parts and laser receiver parts, configured such that a single laser irradiation part transmits laser light to a single laser receiver part, may be provided, and information received by the plurality of laser receiver parts may be processed by only a single control part, as in the third embodiment of FIG. 6. In the case in which a single control part is provided, there is an advantage in that a plurality of pieces of information can be processed at once, but there is a disadvantage in that it takes time to process information. In the case in which a plurality of control parts is provided, on the other hand, there is an advantage in that each piece of information can be rapidly processed, but there is a disadvantage in that it is not possible to compare and analyze a plurality of pieces of information.

The single control part connected to the plurality of laser receiver parts may provide a signal to a single alarm part connected thereto such that the alarm part is operated.

The disposition of the laser unit according to the third embodiment may be applied to all laser units disposed in the battery pack, or the battery pack may be divided into several sections, in each of which a single control part and/or a single alarm part may be provided.

The battery pack according to the present invention is subjected to a gas detection method shown in FIG. 7. FIG. 7 is a flowchart of a gas detection method of a battery pack according to the present invention.

1) After a state in which a laser unit according to the present invention is mounted to the battery pack and normal monitoring is performed (Start), the scattering ratio $\Delta I/I_0$ of laser light received by a laser receiver part is compared with a predetermined scattering ratio a. In the case in which the scattering ratio of the received laser light received by a laser receiver part is equal to or greater than the predetermined scattering ratio (S01, a subsequent step is performed. In the case in which the scattering ratio of the received laser light received by a laser receiver part is less than the predetermined scattering ratio, monitoring is performed again in the state in which time is initialized.

2) After step 1), a step (S02) of adding a measurement time value $\Delta t$ to a previous time value $t_{old}$ to generate a new time value $t_{new}$ is performed.

The time value $t_{new}$ Generated in step 2) is compared with a predetermined time b, and is the case in which the generated time value $t_{new}$ is equal to or greater than the predetermined time b, a step (S03) of generating a signal and advancing to a subsequent step is performed. At this time, in the case in which the generated time value $t_{new}$ is less than the predetermined time b, the generated time value $t_{new}$ is regarded to be the previous time value $t_{old}$, and step S01 is performed again.

4) Gas may be detected through a step of transmitting the signal generated in step 3) to an alarm part so as to provide an alarm signal.

The scattering ratio $\Delta I/I_0$ of the laser light received by the laser receiver part is a value obtained by dividing the intensity of the received laser light by the intensity of initial laser light set as a reference value. The predetermined scattering ratio a is an optical loss value based on gases detected in each battery pack. This may be estimated through the composition of gases generated in a general battery pack.

Thereupon, a fire outbreak test (Experimental Example 1) was performed using a JH4 battery sold by LG Chem, Ltd. in order to confirm the composition of gases. Specifically, gases that are generated may be different in ratio from each other but may be similar to each other in terms of general constituents. The composition of gases generated when a fire breaks out in the JH4 battery is shown in Table 1 below.

In Table 1 below, C4' includes i-C4(isobutane), t-C4 (trans-2-butene), n-C4 (n-butane), cis-C4(cis-2-butene), 1-butene, isobutene, and 1,3-butadiene.

TABLE 1

| Gas | Measured (%) |
| --- | --- |
| $H_2$ | 18.3 |
| CO | 13.9 |
| $CO_2$ | 17.1 |
| $CH_4$ (Methane) | 4.2 |
| $C_2H_4$ (Ethylene) | 2.7 |
| $C_2H_6$ (Ethane) | 0.46 |
| $C_3H_6$ (Propylene) | 0.62 |
| $C_3H_8$ (Propane) | <0.1 |
| $C_3H_4$ (Propadiene) | <0.02 |
| C4' | 0.27 |
| n-$C_5H_{12}$ (Pentane) | <0.02 |

It can be seen from Table 1 above that about 57.6% of burned gas mass is composed of gases that are generally generated in a large amount at the time of combustion. It can be seen therefrom that the JH4 battery of LG Chem, Ltd. was manufactured based on a hydrocarbon standard, and it can be seen that the gas components that are mainly generated can be applied to most batteries. At this time, since constituents (nitrogen and oxygen of air, among the burned gases that were measured shown in Table 1 above, are detected in a general situation, it is necessary to examine the composition of the other burned gases excluding nitrogen and oxygen. Table 2 below shows the composition of burned gases excluding nitrogen and oxygen.

In Table 2 below, C4' includes i-C4 (isobutane), t-C4 (trans-2-butene), n-C4 (n-butane), cis-C4 (cis-2-butene), 1-butene, isobutene, and 1,3-butadiene.

TABLE 2

| Gas | Measured (%) |
| --- | --- |
| $H_2$ | 31.8 |
| CO | 24.2 |
| $CO_2$ | 29.7 |
| $CH_4$ (Methane) | 7.3 |
| $C_2H_4$ (Ethylene) | 4.7 |
| $C_2H_6$ (Ethane) | 0.80 |
| $C_3H_6$ (Propylene) | 1.08 |
| $C_3H_8$ (Propane) | <0.17 |
| $C_3H_4$ (Propadiene) | <0.03 |
| C4' | 0.47 |
| n-$C_5H_{12}$ (Pentane) | <0.03 |

It can be seen that the other gases excluding nitrogen and oxygen are burned gases, such as hydrogen, carbon monoxide, carbon dioxide, methane, ethylene, ethane, and propylene. A gas particle used in the present invention means a gas particle formed using a burned gas as a precursor. It can be seen from the above composition that the composition of gases generated at the time of combustion generates gases each having a particle size like smoke (a diameter of 0.1 μm to 10 μm).

A value obtained by adding a particle extinction coefficient based on wavelength thereto or a value obtained by multiplying an optical path to the extinction coefficient and adding the resultant thereto may be applied to a Mie scattering theory to decide an optical loss value. At this time, an equation according to the following Beer-Lambert Law (Beer's law) may be used.

$$dI = -I_o \sigma dx$$

$$I(x) = I_o \exp(-\sigma x)$$

Here, I(x) indicates the intensity of transmitted light, $I_o$ indicates the intensity of incident light, $\sigma$ indicates the extinction coefficient of aerosol, and x indicates the thickness of an absorption layer. In the case in which integration is performed from before light passes a medium, i.e. a generated gas layer (x=0) to after the light passes the medium (x=X) using the above equation, it is possible to calculate the intensity of the light after passing through the medium, as follows.

It is expected that an optical loss of 2% to 5% will be generated as the result of calculating the optical loss value based on the above equation and the measured gas value. Consequently, the predetermined scattering ratio a of the present invention may be set to 2% to 5% but may be changed depending on the battery pack.

FIG. 8 shows photographs of a fire outbreak test according to the present invention arranged over time.

In a battery pack including seven battery modules attached to each other, each battery module being constituted by eight unit cells, as in Experimental Example 2 of FIG. 8, a fire outbreak source was provided between the fourth battery module (CMA4) and the fifth battery module (CMA5), and the time of propagation of thermal runaway for each module was checked.

As can be seen from FIG. 8, the duration of initial thermal runaway was about 39 minutes 49 seconds, the time of propagation of thermal runaway to about half of the battery modules was 49 minutes, 16 seconds, and a time of about 1 hour was taken until thermal runaway occurred in all of the cells.

Table 3 below shows detailed experimental results thereof.

TABLE 3

| Time (min:second) | Location of cell in thermal runaway |
|---|---|
| 39:49 | CMA 5 |
| 46:30 | CMA 6, CMA 3 |
| 51:54 | CMA 7, CMA 2 |
| 57:00 | CMA 1 |

These may be confirmed through the graph of FIG. 9. FIG. 9 is a graph showing the results of the fire outbreak test according to the present invention.

It can be estimated therefrom that, assuming that the time of propagation of thermal runaway between the modules is about 400 seconds, which is the time of propagation of thermal runaway from CMA5 to CMA6 or CMA3, the time of propagation of thermal runaway between the cells is 50 seconds (400 seconds/8 cell). Consequently, 40 seconds to 60 seconds, which is a time before thermal runaway occurs, may be set to the predetermined time b such that an alarm may be given or the function of the battery may be stopped before thermal runaway occurs in the battery.

Although the present invention has been described in detail, those skilled in the art will appreciate that the detailed description thereof discloses only preferred embodiments of the present invention and thus does not limit the scope of the present invention. Accordingly, those skilled in the art will appreciate that various changes and modifications are possible, without departing from the category and technical idea of the present invention, and it will be obvious that such changes and modifications fall within the scope of the appended claims.

DESCRIPTION OF REFERENCE NUMERALS

100: Battery pack
110: Battery module
120: Rack housing
130: Lower housing
140: Upper housing
200: Laser irradiation part
300: Laser receiver part
400: Control part
500: Alarm part

INDUSTRIAL APPLICABILITY

As apparent from the above description, a battery pack according to the present invention has an advantage in that it is possible to detect a gas generated is a unit cell using light, whereby it is possible to more rapidly sense the generation of the gas than a conventional gas sensor.

In addition, it is possible to directly sense the generated gas and to determine whether an acquired value continues in order to reduce an error, whereby it is possible to more accurately sense the generation of the gas than in other gas sensors.

The battery pack according to the present invention is capable of sensing a gas generated in the battery pack, whereby it is possible to improve safety of the battery pack.

The invention claimed is:

1. A battery pack comprising:
   at least one battery module comprising at least one unit cell;
   a rack housing configured to receive the at least one battery module;
   a lower housing having an inner space in a form in which an upper part of the lower housing is open, the lower housing being configured to receive the at least one battery module in the inner space;
   an upper housing coupled to the upper part of the lower housing, the upper housing having an inner space configured to receive the at least one battery module; and
   at least one laser unit disposed in the rack housing, the at least one laser unit being configured to sense a gas using Mie scattering,
   wherein the at least one laser unit comprises:
     a laser irradiator formed at a first surface of the rack housing, the laser irradiator being configured to irradiate laser light;
     a laser receiver configured to receive the laser light irradiated by the laser irradiator, the laser receiver being formed at a second surface of the rack housing opposite the laser irradiator; and
     a control part configured to compare an intensity of the laser light received by the laser receiver with a reference value in order to determine generation of a gas.

2. The battery pack according to claim 1, wherein the at least one laser unit comprises two or more laser units.

3. The battery pack according to claim 2, wherein the two or more laser units are located parallel to each other with the at least one battery module disposed therebetween.

4. The battery pack according to claim 2, wherein the two or more laser units are located as mirror images with the at least one battery module disposed therebetween.

5. The battery pack according to claim 2, wherein the two or more laser units comprise:
   two or more laser irradiators formed at a first surface of the rack housing, the two or more laser irradiators being configured to irradiate laser light; and
   two or more laser receivers configured to respectively receive the laser light irradiated by the two or more laser irradiators, the two or more laser receivers being formed at a second surface of the rack housing opposite the two or more laser irradiators;
   a single control part connected to the two or more laser units,
   wherein the control part is configured to compare an intensity of the laser light received by the two or more laser receivers with a reference value in order to determine generation of a gas.

6. The battery pack according to claim 1, wherein the laser irradiator is configured to irradiate laser light having a wavelength equal to or less than a size of a gas particle generated in the battery pack.

7. The battery pack according to claim 6, wherein the gas particle has a diameter of 0.1 μm to 10 μm.

8. The battery pack according to claim 1, wherein the at least one laser unit further comprises an alarm.

* * * * *